United States Patent [19]

Hayakawa et al.

[11] Patent Number: 4,539,401
[45] Date of Patent: Sep. 3, 1985

[54] PYRIDOBENZOXAZINE DERIVATIVES USEFUL AS ANTIBACTERIAL AGENTS

[75] Inventors: Isao Hayakawa; Yoshiaki Tanaka, both of Tokyo, Japan

[73] Assignee: Daiichi Seiyaku Co., Ltd., Tokyo, Japan

[21] Appl. No.: 507,652

[22] Filed: Jun. 27, 1983

[30] Foreign Application Priority Data

Jun. 29, 1982 [JP] Japan ................................. 57-112040

[51] Int. Cl.$^3$ ........................................... C07D 498/16
[52] U.S. Cl. .................................................... 544/101
[58] Field of Search ........................... 544/101; 546/89

[56] References Cited

U.S. PATENT DOCUMENTS 4,382,892  5/1983  Hayakawa et al. .................. 544/101

Primary Examiner—Alan L. Rotman
Attorney, Agent, or Firm—Sughrue, Mion, Zinn, Macpeak & Seas

[57] ABSTRACT

Pyridobenzoxazine derivatives of formula (I)

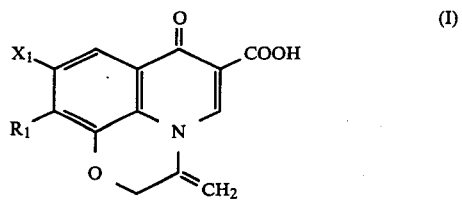

wherein:
$X_1$ represents a hydrogen atom or a halogen atom,
$R_1$ represents a cyclic amino group which may contain additional hetero atom(s) of N,S and O and may be substituted with one or more substituents selected from the group consisting of hydroxyl, amino, alkyl, mono- or di-alkylamino, hydroxyalkyl and aminoalkyl, and physiologically acceptable salts thereof, having antibacterial activity.

5 Claims, No Drawings

PYRIDOBENZOXAZINE DERIVATIVES USEFUL AS ANTIBACTERIAL AGENTS

FIELD OF THE INVENTION

This invention relates to novel pyridobenzoxazine derivatives which are useful as antibacterial agents.

BACKGROUND OF THE INVENTION

European Patent Application (OPI) No. 47005 describes 9-fluoro-10-substituted-3-methyl-7-oxo-2,3-dihydro-7H-pyrido(1,2,3-de)-1,4-benzoxazine-6-carboxylic acid and West German Patent Application (OPI) No. 2914258 describes 9-fluoro-8-(4-methyl-1-piperazinyl)-5-methyl-6,7-dihydro-1-oxo-1H,5H-benz(ij)quinolizine-2-carboxylic acid (the term "OPI" as used herein refers to a "published unexamined application").

The present inventors found that introduction of a methylene group (=CH$_2$) into the tricyclic compounds brought the excellent antibacterial activity and completed this invention.

DETAILED DESCRIPTION OF THE INVENTION

This invention relates to a novel antibacterial agent, and more particularly to pyridobenzoxazine derivatives of formula (I)

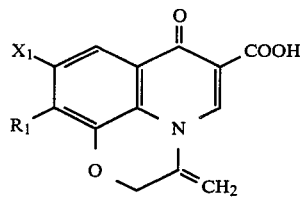

wherein:
$X_1$ represents a hydrogen atom or a halogen atom,
$R_1$ represents a cyclic amino group which may contain additional hetero atom(s) of N, S and O and may be substituted with one or more substituents selected from the group consisting of hydroxyl group, amino group, mono- or di-alkylamino group, aminoalkyl group, hydroxyalkyl group and alkyl group, and physiologically acceptable salt thereof.

In the description of this specification and claims, the alkyl groups have from 1 to 6 carbon atoms.

The cyclic amino group which may contain additional hetero atom(s) of N, S and O refers to groups derived from 4- to 7-membered heterocyclic compounds and examples of such groups include 1-azetidinyl, 1-pyrrolidinyl, 1-piperidinyl, 1-piperazinyl, 4-morpholinyl, 1-homopiperazinyl and the like as well as the substituted groups thereof such as 3-hydroxy-1-pyrrolidinyl, 3-amino-1-pyrrolidinyl, 3-alkylamino-1-pyrrolidinyl and 4-methyl-1-piperazinyl.

The compound of this invention can form an acid addition salt with an inorganic acid such as hydrochloric acid and sulfuric acid or an organic acid such as acidic amino acids, e.g. aspartic acid and glutamic acid, uronic acids, e.g. glucuronic acid and galacturonic acid, sulfonic acids, e.g. methanesulfonic acid, carboxylic acids, e.g. tartaric acid, and the like. Moreover, the compounds of this invention can form the corresponding carboxylate with an alkali metal or an alkaline earth metal such as sodium, potassium, calcium and the like.

The compounds of this invention have excellent antibacterial activity against Gram-positive and Gram-negative bacteria, particularly, against *Pseudomonas aeruginosa*.

Referring to $X_1$ in the structural formula (I), halogen atom, especially, fluorine atom is preferred and referring to $R_1$, substituted pyrrolidinyl group, especially, 3-amino-1-pyrrolidinyl group and 3-hydroxy-1-pyrrolidinyl group are preferred. A particularly preferred class of compounds is those having formula (I) wherein $X_1$ is a fluorine atom and $R_1$ is a 3-hydroxy-1-pyrrolidinyl group or a 3-amino-1-pyrrolidinyl group and the most preferred embodiment is the compound of formula (I) wherein $X_1$ is a fluorine atom and $R_1$ is a 3-amino-1-pyrrolidinyl group.

The process for preparing the compounds of formula (I) is illustrated by the following reaction scheme:

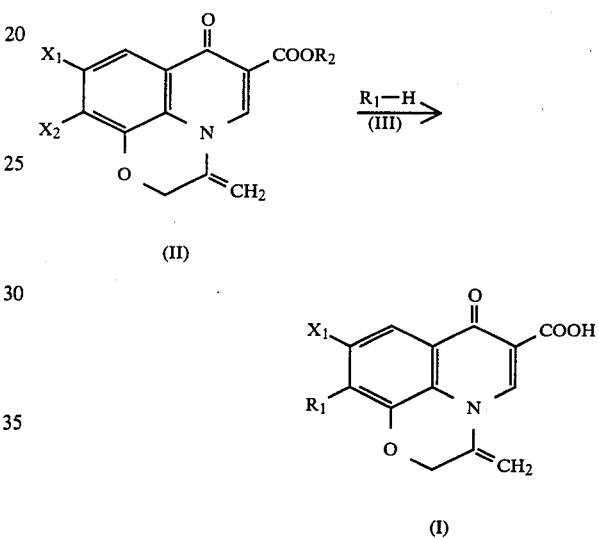

wherein
$X_1$ and $R_1$ are as defined above,
$X_2$ represents a halogen atom,
$R_2$ represents a hydrogen atom or an alkyl group.

The reaction of the compound of formula (II) with the compound of formula (III) is usually performed in the absence of solvent or in the presence of a polar solvent such as water, alcohols, dimethylformamide, dimethylacetamide, dimethyl sulfoxide, pyridine and the like for 1 hour to 6 hours at 50° C. to 200° C., preferably at 100° C. to 150° C. Alternatively, the above reaction can be performed in the presence of an acid acceptor such as a tertiary amine, e.g. triethylamine and dimethylaniline, an inorganic base, e.g. potassium carbonate and the like at a molar ratio of 1.0 to 1.2 of the acid acceptor per mole of the compound of formula (II). When the reaction is performed in the presence of the acid acceptor, the compound of formula (III) can be preferably employed in 1.0 mole to 1.2 moles per mole of the compound of formula (II) and when the reaction is performed in the absence of the acid acceptor, the compound of formula (III) can be preferably employed in 2 moles to 5 moles per mole of the compound of formula (II).

When the compound of formula (III) is a cyclic amine substituted with an amino group, an aminoalkyl group or a mono-alkylamino group, the amino moiety is protected with a protecting group and the protected compound is allowed to react with the compound of formula (II). Thereafter, the protecting group can be eliminated from the resulting compound to produce the objective compound of formula (I).

The reactions used for eliminating the protecting group include a usual hydrolysis with an acid or a base and a usual catalytic reduction.

The hydrolysis is favorable for eliminating such protecting groups as tertiary butoxycarbonyl group, ethoxycarbonyl group, acyl group, e.g. acetyl group and trifluoroacetyl group, tosyl group and the like. And the catalytic reduction is favorable for eliminating such protecting groups as 4-methoxybenzyl group, benzyl group, benzhydryl group and the like.

When the compound of formula (II) wherein $R_2$ is an alkyl group is reacted with the compound of formula (III), the ester moiety of the product can be decomposed by hydrolysis with an acid or a base.

The hydrolysis of ester moiety with a base is usually performed in a solvent such as an aqueous alcohols or a mixture of water and an organic polar solvent, e.g. dimethyl suloxide and dimethylformamide, for 15 minutes to 2 hours at room temperature to 100° C. Examples of the base include an inorganic base such as an alkali metal or alkaline earth metal hydroxide or carbonate and the like. The base is usually employed in an amount of 1 mole to 5 moles per mole of the ester compound.

The hydrolysis of ester moiety with an acid is usually performed by heating the ester compound in an inorganic acid such as hydrochloric acid or a mixture of an inorganic acid and an alcohol such as methanol for 30 minutes to 5 hours under reflux or by heating the ester compound in a mixture of inorganic acid and an organic acid such as acetic acid for 30 minutes to 5 hours at 100° C. to 130° C. The inorganic acid is usually employed in an amount of 2 moles to 10 moles per mole of the ester compound. When the inorganic acid is employed in excess, it can act as a solvent as well.

Apparently from the description with respect to the elimination of protecting group and decomposition of ester moiety, it is possible to complete the above two reactions together by hydrolysis.

The compounds of formula (II) can be prepared by the process outlined below:

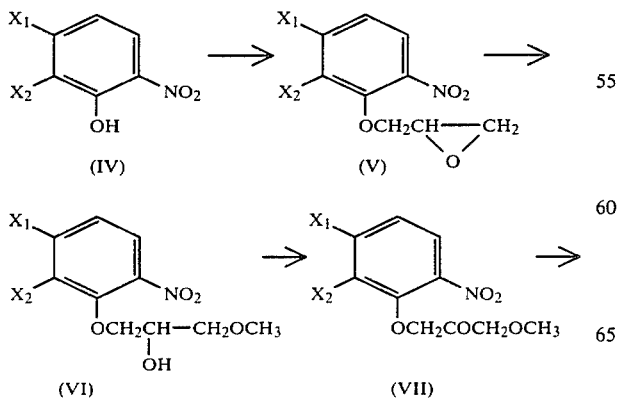

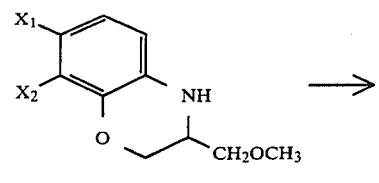

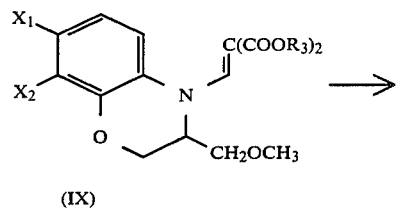

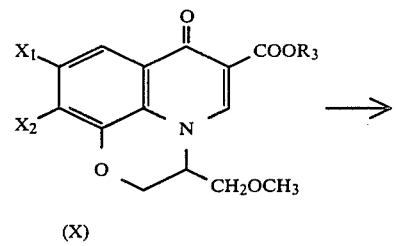

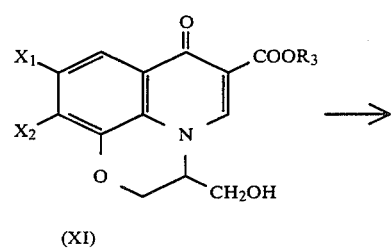

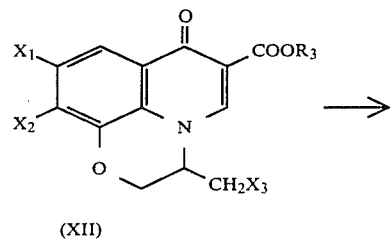

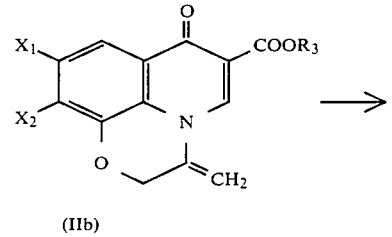

-continued

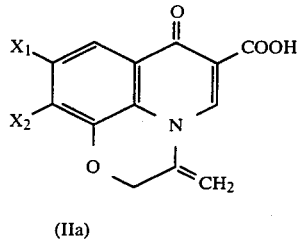

(IIa)

wherein $X_1$ and $X_2$ are as defined above, $X_3$ represents a halogen atom and $R_3$ represents an alkyl group.

That is, the compound of formula (IV) is allowed to react with an epihalogenohydrin in the presence of an acid acceptor such as a tertiary amine, an inorganic base, e.g. potassium carbonate and the like to produce the compound of formula (V) and the product is heated with a catalytic amount of tin dichloride in an alcohol to produce the compound of formula (VI) and then the product is treated with an oxidizing agent containing anhydrous chromic acid such as the Jones reagent to produce the compound of formula (VII). The compound of formula (VII) is reduced in the presence of a catalyst such as Raney nickel, palladium black and the like to produce the compound of formula (VIII) and the product is heated with a dialkyl alkoxymethylenemalonate to produce the compound of formula (IX) and then the product is heated in a polyphosphoric acid or an ester thereof to produce the compound of formula (X). The compound of formula (X) is treated with an aluminum halogenide to produce the compound of formula (XI) and the product is treated with a halogenating agent such as thionyl chloride to produce the compound of formula (XII) and then the product is treated with an acid acceptor such as a tertiary amine, specifically, 1,8-diazabicyclo(5,4,0)-7-undecene, to produce the compound of formula (IIb). The compound of formula (IIb) is hydrolyzed in a similar manner as that used for obtained the objective compound from the ester compound to produce the compound of formula (IIa).

The antibacterial activity of the compounds of this invention is shown in the following Table 1.

TABLE 1

| Test Organism | MIC (mcg/ml)* | |
| --- | --- | --- |
|  | Ia | Ib |
| E. coli, NIHJ | 0.0125 | 0.025 |
| Sh. flexneri, 2a, 5503 | 0.025 | 0.0125 |
| Pr. vulgaris, 08602 | 0.025 | 0.025 |
| Pr. mirabilis, IFO-3849 | 0.05 | 0.025 |
| K. pneumoniae, type 1 | 0.19 | 0.05 |
| Ent. cloacae, 03400 | 0.05 | 0.025 |
| Ser. marcescens, 10104 | 0.10 | 0.05 |
| Ps. aeruginosa, 32104 | 0.78 | 0.10 |
| Ps. aeruginosa, 32233 | 0.78 | 0.19 |
| Ps. aeruginosa, 32234 | 0.78 | 0.10 |
| Ps. aeruginosa, 32121 | 0.19 | 0.05 |
| Ps. aeruginosa, 32122 | 0.78 | 0.10 |
| S. aureus, 209 P | 0.05 | 0.10 |
| S. epidermidis, 56500 | 0.19 | 0.39 |
| Str. pyogenes, G-36 | 0.78 | 0.78 |
| Str. faecalis, ATCC-19433 | 0.39 | 0.78 |
| B. subtilis, ATCC-6633 | ≦0.0063 | 0.05 |

*Determined by the standard method of the Japan Society of Chemoterapy: (Mueller-Hinton Broth medium), $10^6$/ml of bacteria were seeded and incubated at 37° C. for 18 hours.
Ia: 9-fluoro-10-(3-hydroxy-1-pyrrolidinyl)-3-methylene-7-oxo-2,3-dihydro-7H—pyridol(1,2,3-de)-1,4-benzoxazine-6-carboxylic acid
Ib: 10-(3-amino-1-pyrrolidinyl)-9-fluoro-3-methylene-7-oxo-2,3-dihydro-7H—pyrido(1,2,3-de)-1,4-benzoxazine-6-carboxylic acid As can be seen in the Table 1, the compounds of this invention exhibit a very excellent antibacterial activity, particularly, 3-hydroxy-1-pyrrolidinyl compound (Ia) exhibits a very strong antibacterial activity against Gram-positive bacteria and 3-amino-1-pyrrolidinyl compound (Ib) exhibits a very strong antibacterial activity against Pseudomonas aeruginosa. The excellency is clearly comprehensible in comparing the Table 1 with the Tables in the specification of EP Application (OPI) No. 47005 and DE Application (OPI) No. 2914258.

With respect to the toxicity of the compounds of this invention, the acute toxicity (LD 50) of the compound (Ia, sodium salt) is 333 mg/kg and that of the compound (Ib, methanesulfonic acid addition salt) is more than 320 mg/kg as determined in mice (i.v.).

PRODUCTION OF STARTING MATERIAL 7.0 g of 2,3-difluoro-6-nitrophenol, 7.0 g of epichlorohydrin, 15 g of potassium carbonate and 600 mg of potassium iodide were added to 150 ml of dimethylformamide and the mixture was stirred for 20 hours at 85°–90° C. (bath temperature). The insoluble material was removed by filtration and the filtrate was concentrated to dryness in vacuo and then the residue was distributed between chloroform and water. The chloroform layer was washed with water and dried over sodium sulfate. The solvent was distilled off and the residue was purified by silica gel column chromatography to give 6.1 g of 2,3-difluoro-6-nitrophenyl oxyranylmethyl ether as a light yellow oil.

15.0 g of the above product and 0.3 ml of tin dichloride were added to 60 ml of anhydrous methanol and the resulting mixture was refluxed for 2 hours. The solvent was distilled off and the residue was distributed between chloroform and water. 16.1 g of 1-(2,3-difluoro-6-nitrophenoxy)-3-methoxy-2-propanol was obtained as an oil from chloroform layer.

15 g of the above product was dissolved in 150 ml of acetone and 50 ml of the Jones reagent prepared from 32 g of anhydrous chromic acid, 64 ml of water and 16 ml of concentrated sulfuric acid was added dropwise to the mixture under stirring and cooling in an ice bath. The resulting mixture was stirred for 30 minutes at the same temperature and for additional 2 hours at room temperature. The insoluble material was collected by filtration and washed with acetone and chloroform. The washings were combined with the filtrate and the mixture was concentrated to dryness and then the residue was distributed between chloroform and water. The chloroform layer was washed with water and dried over sodium sulfate. The solvent was distilled off and the residue was purified by silica gel column chromatography with chloroform eluent to give 10.6 g of 1-(2,3-difluoro-6-nitrophenoxy)-3-methoxy-2-propanone with mp 39°–42° C.

Analysis for $C_{10}H_9F_2NO_5$; Calculated: C; 45.99, H; 3.47, N; 5.36, Found: C; 45.79, H; 3.26, N; 5.29.

9.5 g of the above product was dissolved in 100 ml of ethanol. After addition of 10 ml of Raney nickel, it was catalytically reduced under normal atmospheric pressure and the catalyst was removed by filtration. The solvent was distilled off in vacuo and the residue was purified by silica gel column chromatography to give 3.9 g of an oily product. 3.5 g of diethyl ethoxymethylenemalonate was added to 3.0 g of the above product and the mixture was heated for 2 hours at 105°–115° C. (bath temperature). The reaction mixture was purified by silica gel column chromatography to give 4.1 g of diethyl (7,8-difluoro-3-methoxymethyl-2,3-dihydro-4H-1,4-benzoxazin-4-yl)methylenemalonate with mp 81° C.

Analysis for $C_{18}H_{21}F_2NO$; Calculated: C; 56.10, H; 5.49, N; 3.64, Found: C; 56.25, H; 5.47, N; 3.74.

3.0 g of the above product was added to 20 g of polyphosphate (prepared from phosphoric anhydride and ethanol) and the mixture was heated for 1.5 hours at 120°–125° C. (bath temperature). Ice-cooled water was added to the reaction mixture and the precipitate formed was extracted with chloroform. The extract was washed with water and dried over sodium sulfate. The solvent was distilled off and the residue was purified by silica gel column chromatography with chloroform eluent and then recrystallized from a mixture of dichloromethane and diisopropyl ether to give 1.7 g of ethyl 9,10-difluoro-3-methoxymethyl-7-oxo-2,3-dihydro-7H-pyrido(1,2,3-de)-1,4-benzoxazine-6-carboxylate with mp 238° C. as fine needles.

Analysis for $C_{16}H_{15}F_2NO_5$; Calculated: C; 56.64, H; 4.46, N; 4,13, Found: C; 56.51, H; 4.44, N; 4.02.

1.7 g of the above product was added to 100 ml of dichloromethane and a mixture of 6.0 g of aluminum bromide and 10 ml of ethanethiol was added dropwise to the mixture under cooling in an ice bath. The temperature of the resulting mixture was raised to room temperature and the mixture was stirred for 3 hours at the same temperature. The solvent was distilled off and ice-cooled water was added to the residue. The precipitate formed was collected by filtration and recrystallized from a mixture of chloroform and ethanol to give 1.1 g of ethyl 9,10-difluoro-3-hydroxymethyl-7-oxo-2,3dihydro-7H-pyrido(1,2,3-de)-1,4-benzoxazine-6-carboxylate with mp 268°–270° C. as fine needles.

Analysis for $C_{15}H_{13}F_2NO_5$; Calculated: C; 55.39, H; 4.03, N; 4.31, Found: C; 55.66, H; 4.23, N; 4.29.

400 mg of the above product was dissolved in 30 ml of chloroform and 3 ml of thionyl chloride was added to the mixture. The resulting mixture was refluxed for 4 hours. The reaction mixture was concentrated to dryness in vacuo and the residue was dissolved in chloroform. The mixture was washed with water, an aqueous solution of sodium bicarbonate and water and then dried over sodium sulfate. The solvent was distilled off and the residue was recrystallized from a mixture of chloroform and ethanol to give 220 mg of ethyl 3-chloromethyl-9,10-difluoro-7-oxo-2,3-dihydro-7H-pyrido)1,2,3-de)-1,4-benzoxazine-6-carboxylate with mp 250°–251° C. as fine needles.

Analysis for $C_{15}H_{12}ClF_2NO_4$: Calculated: C; 52.42, H; 3.52, N; 4.08, Found: C; 52.26, H; 3,45, N; 4.10.

200 mg of the above product was suspended in 30 ml of anhydrous benzene and 230 mg of 1,8-diazabicyclo(5,4,0)-7-undecene was added to the mixture and then the resulting mixture was refluxed for one hour. Chloroform was added to the reaction mixture and the mixture was washed with water and dried over sodium sulfate. The solvent was distilled off and the residue was purified by silica gel column chromatography and recrystallized from a mixture of dichloromethane and diisopropyl ether to give 120 mg of ethyl 9,10-difluoro-3-methylene-7-oxo-2,3-dihydro-7H-pyrido(1,2,3-de)-1,4-benzoxazine-6-carboxylate with mp 258°–263° C.

NMR(DMSO-$d_6$, $\delta$ ppm); 5,47, 5,89 (each 1H, d, J=2.5 Hz, $C_3$=$CH_2$).

Analysis for $C_{15}H_{11}F_2NO_4$: Calculated: C; 58.64, H; 3.61, N; 4.56, Found: C; 58.22, H; 3.33, N; 4.47.

EXAMPLE 1

100 mg of ethyl 9,10-difluoro-3-methylene-7-oxo-2,3-dihydro-7H-pyrido(1,2,3-de)-1,4-benzoxazine-6-carboxylate was dissolved in 3 ml of dimethyl sulfoxide and 100 mg of N-methylpiperazine was added to the mixture and then the resulting mixture was stirred for 6 hours at 120°–130° C. (bath temperature). The solvent was distilled off in vacuo and the residue was purified by silica gel column chromatography to give 100 mg of a powder. The powder was suspended in 10 ml of ethanol and 1 ml of 3% aqueous solution of sodium hydroxide was added to the mixture. The resulting mixture was stirred for 30 minutes at 40°–50° C. The reaction mixture was concentrated to dryness in vacuo and water was added to the residue. The mixture was acidified by addition of diluted hydrochloric acid and was made basic with sodium bicarbonate and then extracted with chloroform. The extract was dried over sodium sulfate and the solvent was distilled off. The residue was purified by silica gel column chromatography and recrystallized from ethanol to give 25 mg of 9-fluoro-10-(4-methyl-1-piperazinyl)-3-methylene-7-oxo-2,3-dihydro-7H-pyrido(1,2,3-de)-1,4-benzoxazine-6-carboxylic acid with mp 200°–201° C. as fine needles.

NMR (CDCl$_3$, $\delta$ ppm), 4.83 (2H, S, $C_2$—$H_2$), 5.26,5.61 (each 1H, d, J=3.0 Hz, $C_3$=$CH_2$), 8.83 (1H, s, $C_5$—H), 7.63 (1H, d, J=12 Hz, $C_8$—H).

Analysis for $C_{18}H_{18}FN_3O_4.\frac{1}{2}H_2O$; Calculated: C; 58.69, H; 5.20, N; 11.41, Found: C; 58.98, H; 4.97, N; 11.35.

EXAMPLE 2

900 mg of ethyl 9,10-difluoro-3-methylene-7-oxo-2,3-dihydro-7H-pyrido(1,2,3-de)-1,4-benzoxazine-6-carboxylate was suspended in 20 ml of ethanol and 5 ml of an aqueous solution containing 500 mg of potassium hydroxide was added thereto. The resulting mixture was allowed to react for 3 hours at 50°–60° C. (bath temperature). The solvent was distilled off and 10 ml of water was added to the residue and the mixture was neutralized by addition of hydrochloric acid. The precipitate formed was collected by filtration and washed with water and then dried to give 810 mg of 9,10-difluoro-3-methylene-7-oxo-2,3-dihydro-7H-pyrido-(1,2,3-de)-1,4-benzoxazine-6-carboxylic acid as a white powder. The powder was recrystallized from ethanol to give fine needles with mp 273°–276° C. (decomposition).

NMR(DMSO-$d_6$, $\delta$ ppm), 5.14 (2H, s, $C_2$-$H_2$), 5.66, 6.13 (each 1H, d, J=2Hz, $C_3$=$CH_2$).

Analysis for $C_{13}H_7F_2NO_4$: Calculated: C: 55.92, H: 2.53, N: 5.02, Found: C: 55.69, H: 2.70, N: 4.93.

100 mg of the above product and 200 mg of 3-hydroxypyrrolidine were added to 3 ml of dimethyl sulfoxide and the mixture was stirred for 6 hours at 120°–130° C. (bath temperature). The solvent was distilled off in vacuo and the residue was washed twice with water and with a mixture of diethyl ether and ethanol (4:1 by volume) and then dried to give a yellow powder. The powder was recrystallized from ethanol to give 72 mg of 9-fluoro-10-(3-hydroxy-1-pyrrolidnyl)-3-methylene-7-oxo-2,3-dihydro-7H-pyrido(1,2,3-de)-1,4-benzoxazine-6-carboxylic acid as yellow needles with mp 288°–289° C. (decomposition).

Analysis for $C_{17}H_{15}FN_2O_5$: Calculated: C: 58.96, H: 4.37, N: 8.09, Found: C: 59.07, H: 4.63, N: 8.01.

EXAMPLE 3

130 mg of 9,10-difluoro-3-methylene-7-oxo-2,3-dihydro-7H-pyrido(1,2,3-de)-1,4-benzoxazine-6-carboxylic acid and 300 mg of 3-tertiary-butoxycarbonylaminopyrrolidine were added to 3 ml of dimethyl sulfoxide and the mixture was allowed to react for 3 hours at 100°–110° C. (bath temperature). The solvent was distilled off in vacuo. The residue was washed with diethyl ether and purified by silica gel column chromatography and then recrystallized from benzene to give 125 mg of 10-(3-tertiary-butoxycarbonylamino-1-pyrrolidinyl)-9-fluoro-3-methylene-7-oxo-2,3-dihydro-7H-pyrido(1,2,3-de)-1,4-benzoxazine-6-carboxylic acid with mp 219°–220° C. as luster yellow crystals.

80 mg of the above product was dissolved in 2 ml of trifluoroacetic acid and 1 ml of anisole was added to the mixture and then the resulting mixture was allowed to stand overnight at room temperature. The reaction mixture was concentrated to dryness in vacuo and an aqueous solution of sodium bicarbonate was added to the residue until the mixture became weakly basic. The precipitate formed was collected by filtration and washed with water. The pricipitate was dried and recrystallized from a large amount of a mixture of chloroform and ethanol to give 45 mg of 10-(3-amino-1-pyrrolidinyl)-9-fluoro-3-methylene-7-oxo-2,3-dihydro-7H-pyrido(1,2,3-de)-1,4-benzoxazine-6-carboxylic acid as light yellow needles with mp 260°–265° C. (decomposition).

NMR (DMSO-$d_6$, $\delta$ ppm), 4.83 (2H, s, $C_2$—$H_2$), 5.16, 5.55 (each 1H, $C_3$=$CH_2$).

Analysis for $C_{17}H_{16}FN_3O_4 \cdot \frac{1}{2}H_2O$: Calculated: C: 57.63, H: 4.83, N: 11.86, Found: C: 58.03, H: 4.78, N: 11.90.

EXAMPLE 4

600 mg of 10-(3-amino-1-pyrrolidinyl)-9-fluoro-3-methylene-7-oxo-2,3-dihydro-7H-pyrido(1,2,3-de)-1,4-benzoxazine-6-carboxylic acid was suspended in a mixture of 20 ml of wter and 20 ml of methanol and then 2.2 ml of 1 normal hydrochloric acid was added thereto to give a yellow solution. Insoluble material was removed by filtration and the filtrate was concentrated to dryness in vacuo. 30 ml of ethanol and 20 ml of diethyl ether were added to the residue in a slurry form. The precipitate formed was collected by filtration and washed with diethyl ether and then dried for 30 hours at 70°–80° C. under reduced pressure (1 mm Hg) to give 600 mg of the corresponding hydrochloric acid salt as yellow fine needles. The salt melted at 270°–285° C. with gradual decomposition.

Analysis for $C_{17}H_{16}FN_3O_4 \cdot HCl \cdot \frac{1}{4}H_2O$: Calculated: C: 52.86, H: 4.50, N: 10.88, Found: C: 52.75, H: 4.51, N: 10.87.

EXAMPLE 5

220 mg of 10-(3-amino-1-pyrrolidinyl)-9-fluoro-3-methylene-7-oxo-2,3-dihydro-7H-pyrido(1,2,3-de)-1,4-benzoxazine-6-carboxylic acid was suspended in 10 ml of ethanol and 10 ml of an ethanol solution containing 100 mg of methanesulfonic acid was added dropwise thereto at room temperature under stirring. The resulting mixture was stirred for 15 minutes at 50°–60° C. and then the reaction mixture was concentrated to dryness at room temperature. The yellow residue was washed with anhydrous ethanol and then dried for 40 hours at 60° C. under reduced pressure (1 mm Hg) to give 250 mg of the corresponding methanesulfonic acid salt as a yellow powder with mp 263°–265° C. (decomposition).

Analysis for $C_{17}H_{16}FN_3O_4 \cdot CH_3SO_3H$: Calculated: C: 48.98, H: 4.57, N: 9.52, Found: C: 49.20, H: 4.60, N: 9.55.

What is claimed is:

1. A benzoquinolizine derivative of formula (I)

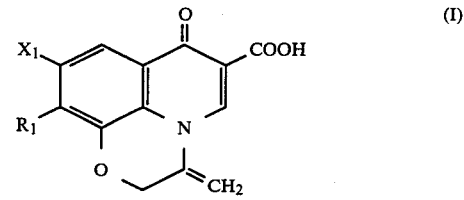

wherein:

$X_1$ represents a hydrogen atom or a halogen atom, $R_1$ represents 1-pyrrolidinyl or 1-piperazinyl which may be substituted with one substituted selected from the group consisting of a hydroxyl group, an amino group and an alkyl group having from 1 to 6 carbon atoms, and physiologically acceptable salts thereof.

2. A compound as claimed in claim 1, wherein $X_1$ is a fluorine atom.

3. A compound as claimed in claim 1, wherein $X_1$ is a fluorine atom and $R_1$ is a substituted pyrrolidinyl group.

4. A compound as claimed in claim 1, wherein $X_1$ is a fluorine atom and $R_1$ is a 3-hydroxy-1-pyrrolidinyl group.

5. A compound as claimed in claim 1, wherein $X_1$ is a fluorine atom and $R_1$ is a 3-amino-1-pyrrolidinyl group.

* * * * *